United States Patent [19]

Maeda

[11] 4,364,593

[45] Dec. 21, 1982

[54] OBJECT GRASPING SYSTEM

[75] Inventor: Yuji Maeda, Kashiwa, Japan

[73] Assignees: Agency of Industrial Science & Technology; Ministry of International Trade & Industry, both of Tokyo, Japan

[21] Appl. No.: 200,912

[22] Filed: Oct. 27, 1980

[30] Foreign Application Priority Data

Oct. 25, 1979 [JP]  Japan ............................... 54-138054

[51] Int. Cl.³ .......................... A61F 1/06; B25J 15/00
[52] U.S. Cl. ....................................... 294/106; 3/12.7
[58] Field of Search ................. 294/86 R, 88, 99 R, 294/106, 111; 3/12, 12.6–12.8; 74/25, 29, 30, 32, 37, 89, 89.11, 89.12, 89.2, 89.21

[56] References Cited

U.S. PATENT DOCUMENTS

| | | | |
|---|---|---|---|
| 2,540,375 | 2/1951 | Motis | 3/12.7 |
| 2,549,716 | 4/1951 | Simpson | 3/12.7 |
| 2,847,678 | 8/1958 | Opuszenski | 3/12.7 |
| 3,694,021 | 9/1972 | Mullen | 294/106 |
| 4,094,016 | 6/1978 | Eroyan | 3/12.7 X |

*Primary Examiner*—Johnny D. Cherry
*Attorney, Agent, or Firm*—Kurt Kelman

[57] ABSTRACT

A widely applicable object grasping system for driving mechanical fingers, wherein a motion converting means for converting the rotary motion of a constant speed motor into linear motion and producing variable-speed motion so as to cause the mechanical fingers to approach an object at a higher speed and to grasp the object at a lower speed with increased moment.

5 Claims, 6 Drawing Figures

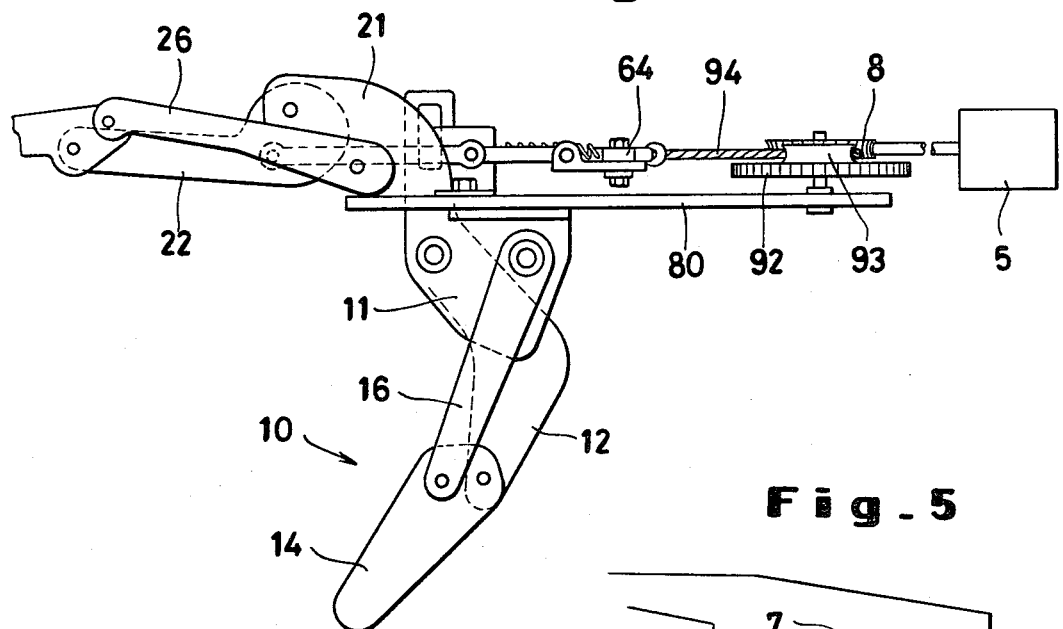
Fig_4
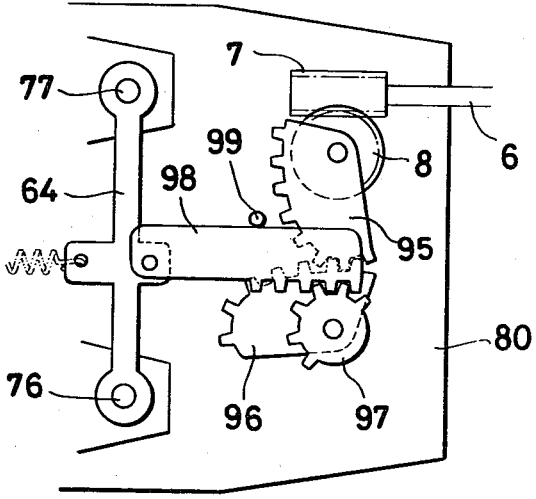
Fig_5
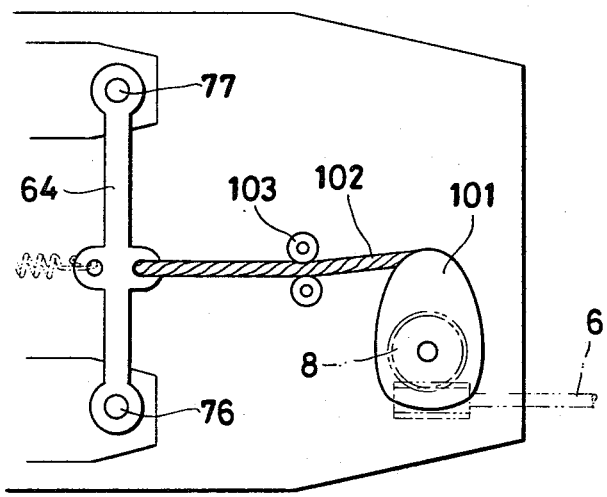
Fig_6

OBJECT GRASPING SYSTEM

BACKGROUND OF THE INVENTION

1. Field of the Invention

The present invention relates to an object grasping system for automatic devices or artificial hands, and more particularly concerned with such a system wherein ideal variable-speed grasping motion is performed by mechanical fingers.

2. Description of the Prior Art

The great development of automatic devices such as industrial robots and artificial hands has resulted from various attempts to embody more reliable performance in these devices. It is very well known that the function of the automatic devices can be improved by the aid of highly efficient computers. In fact computer controlled automatic devices accurately guide working components such as a mechanical arm or hand system in their action to cause mechanical fingers to approach and properly hold an object in the required manner. Some of the latest developments are characterized by close similarity of operation to the human hand in which the mechanical hands dexterously handle objects. Among various other proposed devices, one type of fairly interesting which is so designed that the mechanical fingers of the system are first activated to approach the object at a high speed, and then movement of the mechanical fingers is automatically decreased in speed so that the fingers can grasp the object at a lower speed. This type of device has a particularly ideal feature in that the fingers approach the object at a high speed so as to save operation time, then in order to get a firm grasp of the object at a suitably lower speed with increased moment on the surface of the object, the movement of the fingers is caused to decrease in speed. There are various devices known as means for causing the mechanical hand system to operate at decreasing speed. Conventionally, these means have involved use of variable speed motors. However, the known mechanical hand systems utilizing variable speed motors as means for operating the mechanical hand system at changing speed require complex control systems, and have resulted in greater mechanical complications. As an alternative means, it is possible to use a mechanical hand system design composed of link mechanism wherein a mechanical link construction is so designed to achieve the effect of approaching the object with fingers at a high speed and actually grasping it at decreased speed and with increased moment upon the object. It is, however, not difficult to see that this mechanism also would necessarily be of complex design and require precision control means in establishing the desired performance.

Thus, although prior art mechanical hand systems having control means for attaining the desired mechanical functions have been developed to a fairly high degree of reliability, they are found to be undesirable in view of their complexity and the resulting large weight and size. In many applications, such as in artificial hands where light weight and small size are essential, this proves to be a great disadvantage. Furthermore, most of these mechanical hand systems of highly complicated design are prone to mechanical failure and increased maintenance problems because of the large number of components from which they are composed. Eventually, they have come to be regarded practically as unacceptable.

SUMMARY OF THE INVENTION

It is a principal object of the present invention to provide a unique object grasping mechanism in which the mechanical hand brings its fingers to approach the object at a high speed until just before the hand is about to grasp the object, and then completes the grasp of the object at a lower speed, and with correspondingly increased moment so as to secure a firm grasp of the object.

It is another object of this invention to provide such an object grasping mechanism of light weight and small size and simple in construction.

It is still another object of this invention to provide a reliable object grasping mechanism without the need for conventional complicated control means.

For the purposes of attaining the above objects, the subject system according to the present invention comprises a constant speed motor, a motion conversion means for converting the rotary motion of the motor into a variable-speed linear motion with different speeds, a link mechanism adapted for transmitting the linear motion, and a finger assembly connected with the link mechanism for grasping an object.

The motion conversion means may, for example, be composed of a stepped toothed rack movably disposed for engagement with an associated stepped wheel or a pair of non-circular (e.g., elliptical) gears, operated by the motor through a drive shaft. In the case of a stepped toothed rack and wheel, the rotary motion of the motor is converted into linear motion between the rack and wheel in movement. The pair of non-circular gears requires some suitable means to convert rotary motion to linear motion as will be exemplified later in the description. In either instance, the desired operation of the mechanical fingers holding the object at decreased speed and with inversely proportional increased moment on the object is achieved without the need for complicated structural design.

Many other advantages, features and additional objects of the present invention will become clear to those versed in the art upon making reference to the detailed description and the accompanying drawings in which preferred embodiments incorporating the principles of the present invention are shown by way of illustrative examples.

BRIEF EXPLANATION OF THE DRAWINGS

FIG. 4 is a schematic end view of the object grasping mechanism in FIG. 2;

FIG. 5 is a sectional plan view of a third embodiment of the object grasping system of this invention; and FIG. 6 is a sectional plan view of a fourth embodiment of the object grasping system constructed in accordance with the present invention.

DESCRIPTION OF THE PREFERRED EMBODIMENTS

The present invention relates to an object grasping system which is simple in construction and capable of operating the mechanical hand at variable speed.

Figure 1:
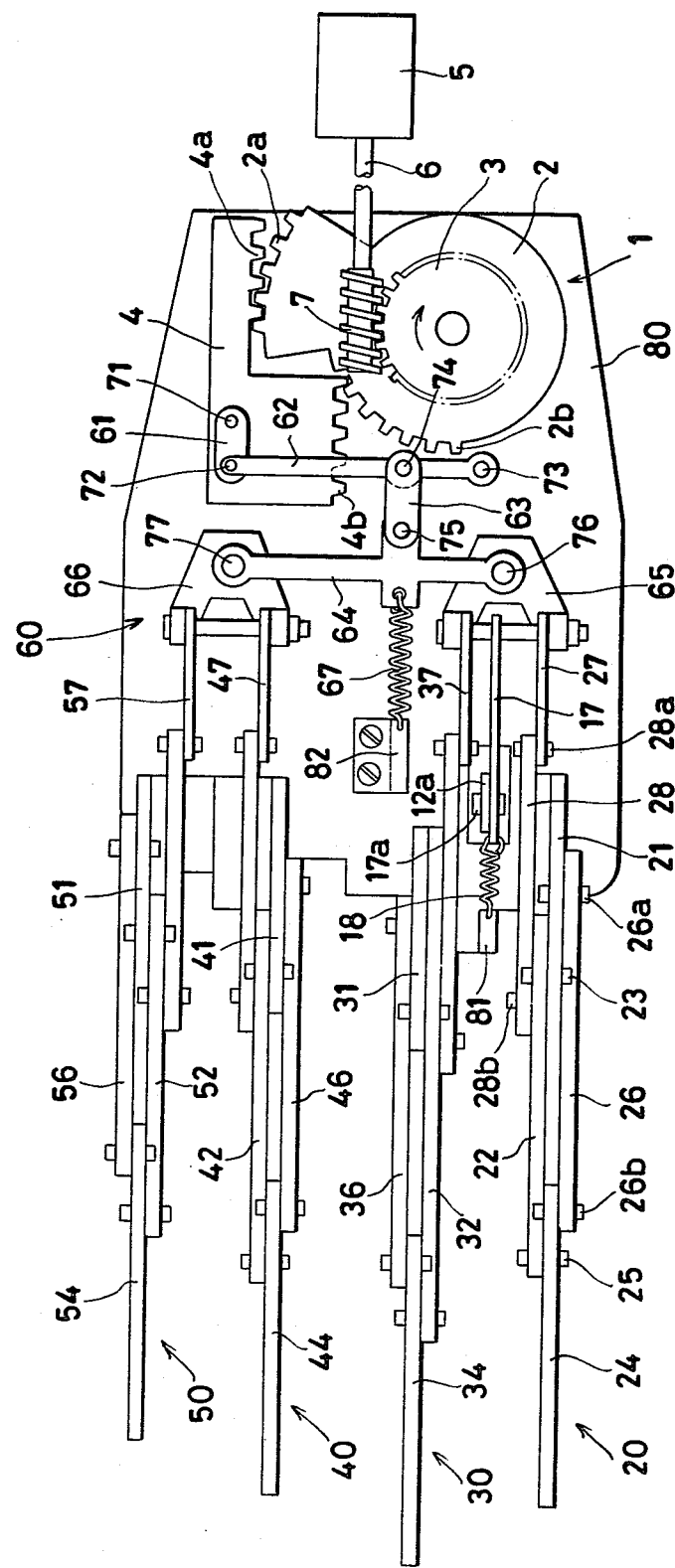
FIG. 1 is a schematic plan view of a first embodiment of the object grasping system according to the present invention.
Figure 2:
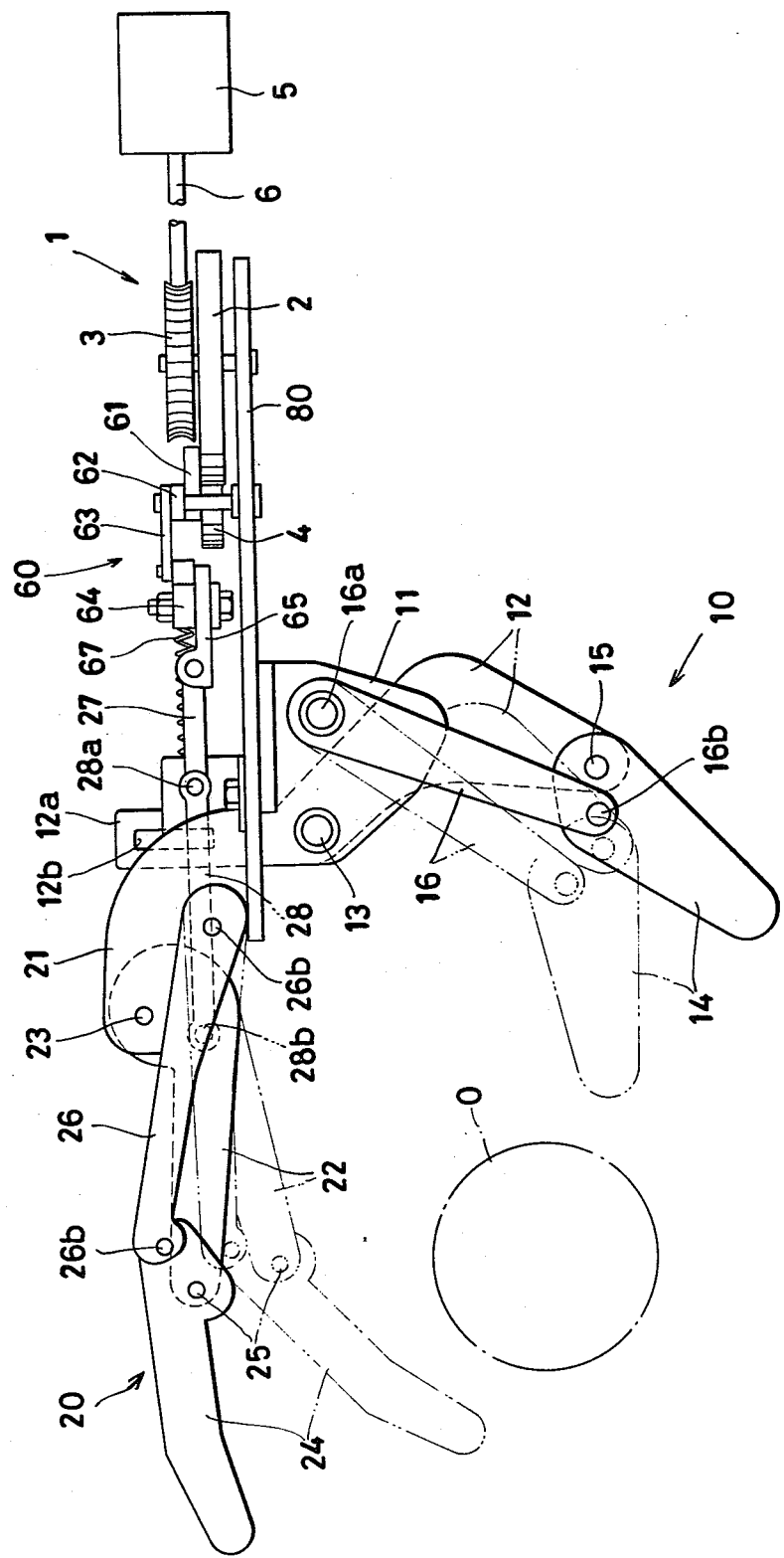
FIG. 2 is a schematic end view of the object grasping system in FIG. 1.

Referring first to FIGS. 1 and 2, there is schematically illustrated a first embodiment of the object grasping system constructed in accordance with the present invention. The object grasping system in the form of a human hand comprises a finger assembly having five mechanical fingers disposed longitudinally which are defined herein as the 1st, 2nd, 3rd, 4th and 5th fingers 10, 20, 30, 40 and 50, which correspond to the thumb through little finger of the human hand, respectively. These mechanical fingers are arranged in the form of link mechanism, and are supported at their respective proximal ends on a base 80 in a manner to be described. The 2nd, 3rd, 4th, and 5th fingers 20, 30, 40 and 50, respectively, are arranged substantially in parallel to each other and are rotatable in the same common direction towards the 1st finger 10 which is disposed for rotation in the opposite direction towards the rest of the fingers 20, 30, 40 and 50 so that the fingers rotate to hold the object positioned between them. The 1st finger 10 has its first link 12 rotatably connected to the base 80 by means of a pivot pin 13, and the first link 12, in turn, is at its opposite end rotatably connected to one end of a second link 14 by means of a pivot pin 15. A control link 16 has its ends connected to a support 11 and to the second link 14 by means of pivot pin 16a and 16b, respectively.

The free end of the first link 12 penetrates through the base 80 to form a projection 12a having an elongated hole 12b therein above the base surface. Slidably engaged into the hole 12b is one end of coupler 17 through the intermediary of a pin 17a in such a manner that linear movement in the coupler 17 causes the link assembly of the 1st finger 10 to turn in the clockwise or counter-clockwise direction. That is, as the coupler 17 retracts pulling at the projection 12a to rotate the first link 12 counter-clockwise about the pivot pin 13, the control link 16 is rotated about the pivot 16a at the support 11, rotating the second link 14 into the position as shown by the phantom line in FIG. 2. The coupler 17 is biased to the left as viewed in the figure by a compression spring 18 fixed to a spring retainer 81 on the base 80.

One of the features that distinguishes the device of the present invention is that the mechanical fingers are designed to operate in a manner quite similar to the human hand, and this will be clearer from a reading of the following description. Most of the prior art mechanical hand systems consist typically of a two-finger assembly which is limited only to the holding of an object of simple shape. There are some other mechanical hands having a three-finger assembly which are suited to holding an object of more complicated configuration without the danger of dropping until the time of release. On the other hand, devices including a five-finger unit have rarely appeared since they have so far been regarded as unacceptable for several reasons. For example, they were thought incapable of holding an object of complicated shape for the reason that it is very difficult to cause each finger to press on the surface of the object with equally regulated force so as to enable the hand to grasp or keep its hold. The present invention is intended to overcome this problem of the prior art by utilizing a link mechanism provided with a dynamic function by a specially designed gear arrangement.

The mechanical hand system according to the present invention will be described in more detail. Since the fingers 20, 30, 40 and 50 are all substantially the same in structure and function, a description which will be made in connection with only the 2nd finger 20 on the understanding that the same description also applies to the other fingers 30, 40 and 50.

The 1st finger 20 has its first link 22 rotatably connected to the base 80 by means of a pivot pin 23, and the first link 22 is rotatably connected at its opposite end to the second link 24 through a pivot pin 25. A control link 26 has its ends rotatably connected to a support 21 and a second link 24 by means of pins 26a and 26b, respectively. An actuator link 28 is rotatably connected to the first link 22 by means of a pivot pin 28b situated slightly nearer to the base 80 than the position of the pivot pin 23 which joins the support 21 with the first link 22. The opposite end of the actuator link 28 is rotatably connected to the coupler 27 through a pin 28a so as to transmit linear movement of the coupler 27 to the 2nd finger 20. Assuming now that the coupler 27 retracts, the first link 22 is rotated about the pivot pin 23 causing the control link 26 to rotate the second link 24 about the pivot pin 25 into the position as shown in a phantom line in FIG. 2 so that the 2nd finger 20 follows to rotate toward the 1st finger 10, and if the two fingers have an object 0 properly placed therebetween and are activated at the same time, the two fingers will approach the object.

As mentioned earlier, the other fingers 30, 40 and 50 are substantially idential in construction and action with the 2nd finger 20. Therefore, by considering the above description in connection with the relative portions of the figure it is easy to see the correspondance between the support 21 of the 2nd finger 20 and supports 31, 41 and 51 in the other fingers, between the first link 22 and first links 32, 42 and 52, between the second link 24 and second links 34, 44 and 54, between the control link 26 and the control links 36, 46 and 56, and between the actuator link 27 and actuator links 37, 47 and 57. Each of the actuator links 27, 37, 47 and 57 disposed for actuating an associated finger link is at its one end joined to actuator shanks 65 and 66. A link divider 64 interconnects the shanks 65 and 66. Linear movement acting on the link divider 64 is divided between shanks 65 and 66 which, in turn, activate the fingers 20, 30, 40 and 50 through the actuator links to rotate counter-clockwise. The arrangement of the shanks 65 and 66 and the divider 64 is such that the linear motion created therethrough is transferred through actuator links 17, 27, 37, 47 and 57 equally into each mechanical finger so that the fingers can press on the surface of the object with even force. A compression spring 67 is provided to bias the divider toward the direction of the finger assembly, which spring serves to maintain each finger in its stretched position when power is not actuated through the link mechanism.

This embodiment of the present invention has a driving section 1 and a power transmission section 60 mechanically connected to the finger unit. Conventional mechanical hand systems typically comprise a motor and a motion converting means adapted for converting the rotary motion of the motor into linear motion. These arrangements required a control means, such as an electric control device, to regulate the speed of the motors when it was necessary to actuate the mechanical hand system to move faster and slower with the required timing. The mechanical hand system according to the present invention has a link mechanism connected with a constant speed motor which is capable of causing the mechanical hand to act, first, at a high speed and then at a low speed without the use for any special electric control means.

The first embodiment of the present invention includes the motion converting means through which the rotary motion of the constant speed motor is converted into variable-speed linear motion. This converting means is a main feature of the invention in that it enables the mechanical fingers to grasp the object at a lower speed than that at which the fingers approach it, without utilizing any particular control means and with a simple structural design. In this embodiment, the converting means is composed of a combination of a longitudinally movable stepped rack 4 and a stepped gear 2 in gear engagement therewith. The rack 4 has two tooth trains 4a and 4b while the stepped gear 2 has two circular gear trains 2a and 2b which engaage with tooth trains 4a of the rack 4. By virtue of the stepped rack 4 in gear engagement with the stepped gear, linear motion with the desired change of speed is derived from the rotary motion of the motor. As the constant speed motor 5 drives the drive shaft 6, a worm 7 at the end of the shaft rotates a worm wheel 3 formed integrally with the stepped gear 2. When the stepped gear 2 rotates clockwise, the first circular gear train 2a moves the first tooth train 4a at a higher speed to the right as viewed in the drawing. The stepped wheel continues on, the second circular gear train 2b begins to engage the second tooth train 4b and follows through to move it further at a lower speed. This is because the speed at a point in a rotating pitch circle increases with increasing the pitch radius of the wheel. In this embodiment, although the stepped wheel and rack are used as a means of producing variable speed linear motion, various other types and forms of gears can also be used to attain the same effect.

Accordiing to the present invention, there is provided the power transmission section 60 for transmitting linear motion from the driving section 1 to the link mechanism, which transmission section comprises a lever arm 62 mounted at its one end on the base 80 to be swingable about a pin 73. The opposite end of the lever arm 62 is pivotally connected to a regulating link 61 attached to the rack 4 by means of a pivot 71. An intermediate portion of the lever arm 62 is interconnected with a link divider 64 via a coupling link 63 and pivot pins 74 and 75. The link 63 is thus free to swing. Moreover, the link divider 64 interconnects the actuator shanks 65 and 66 through pivot pins 76 and 77, so that the divider 64 is also free to swing. A compression spring 67 fixed on a spring retainer 82 on the base 80 is connected to the divider to urge it towards the direction of the mechanical finger unit.

Each finger of the mechanical finger assembly, actuated by the connector links 17 to 57 to which the actuator shanks 65 and 66 are attached, approaches the object at a higher speed while the first circular gear train 2a of the stepped gear 2 is engaged with the first tooth train 4a of the rack 4 and then grasps the object at a lower speed when the second circular gear train 2b is engaged with the second tooth train 4b.

Figure 3:
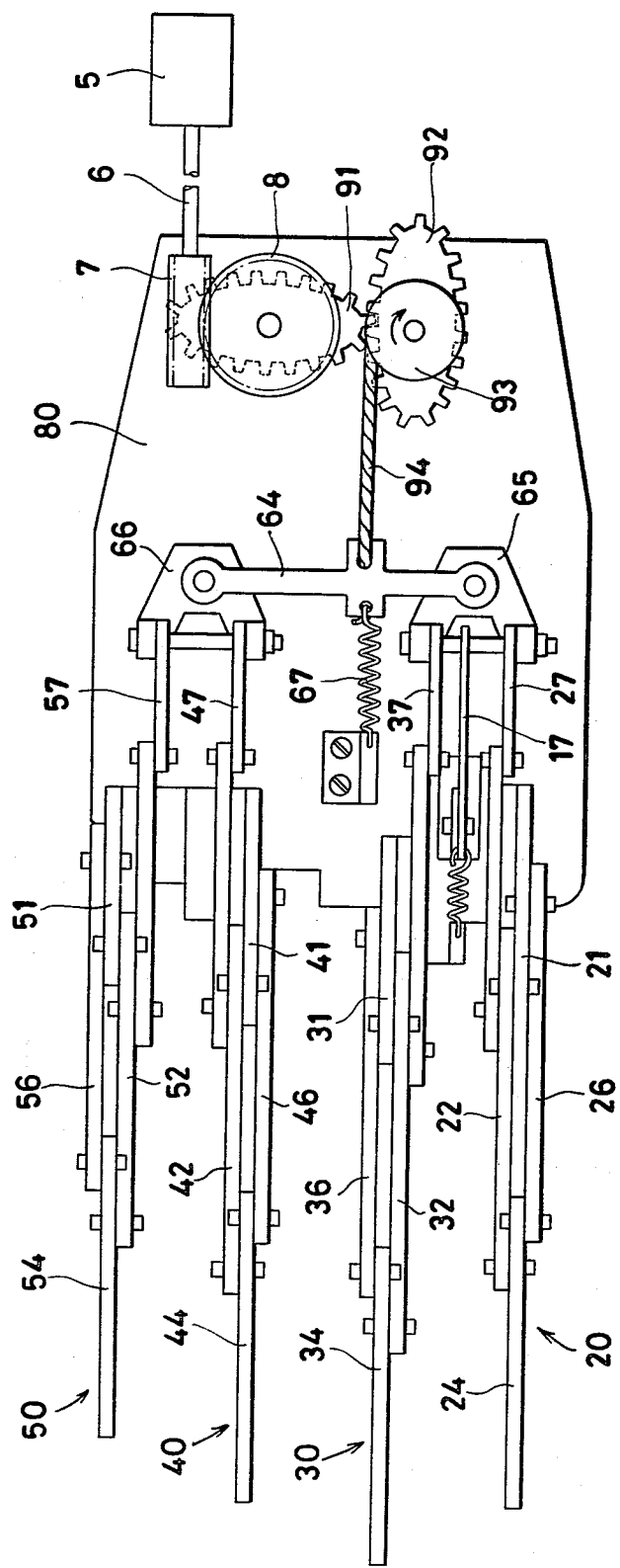
FIG. 3 is a schematic plan view of a second embodiment of the object grasping system of the invention.

Referring now to FIGS. 3 and 4, there is schematically illustrated a second embodiment of the object grasping system according to the invention which is substantially identical in construction to the first embodiment except that a pair of non-circular gears 91 and 92 replace the combination of a stepped rack and a stepped wheel in the first embodiment. Accordingly, like parts are indicated by like reference numerals in this embodiment wherein the constant speed motor 5 is connected through a worm 7 to a worm gear 8 which is formed integrally with a non-circular driving gear 91 to be coaxial therewith. The non-circular gear 91 is set to engage with another non-circular following gear 92 in such a manner that the driving gear 91 driven by the motor 5 rotates the gear 92 first at a higher speed then at a lower speed due to the effect of their shape and relative positions. To convey the linear motion from the motion converting means to a link divider 64 connected to shanks 65 and 66, the non-circular following gear 92 has a driving wheel 93 made integral and coaxial therewith. A connector means 94 is connected at its one end to the driving wheel 93 so as to wind it on the driving wheel 93 and at the other end to the link divider 64. As the driving gear 91 is rotated by the action of the motor 5 through the worm gear 8, the following gear 92 rotates clockwise winding the connector means 94 on the driving wheel 93. The speed of rotation developed in the driving wheel 93 decreases continuously as the non-circular driving gear 91 rotates, thereby causing a continuous decrease in speed of the motion of the finger assembly. In this embodiment, a wire connected to the link divider 64 may be used as a connector means.

The mechanical hand system of this second embodimentis suitable for handing an object of soft material or objects of various forms by using pressure sensor means adapted for feedback control to regulate the amount of the pressure exerted by each mechanical finger upon the surface of object to be gripped.

Referring to FIG. 5, there is schematically illustrated a sectional plan view of a third embodiment of the present invention which is a modified form of the second embodiment. In this embodiment, the driving wheel 93 and connector means 94 used in the second embodiment are replaced by a combination of a pinion 97 and a rack 98. The embodiment is further provided with a pair of sectional toothed gears 95 and 96 which correspond to the effective tooth portions of the gears 91 and 92 of the second embodiment, as is shown in the FIG. 5. To prevent the rack 98 to be released from the pinion 97, a guide pin 99 is disposed on the base 80 so as to be in contact with one side of the rack 98 as illustrated in FIG. 5. The structure of other mechanisms and components is substantially identical with the previous embodiments.

Referring to FIG. 6, there is schematically illustrated a sectional plan view of a fourth embodiment of the present invention which includes a non-circular cam 101 with one end of a wire 102 wound on the circumferential face thereof and a worm gear 8 disposed integrally and coaxially with the cam 101 for rotation. The wire 102 is joined at its other end with a link divider 64 and maintained taut by the force of a spring which urges the divider 64 to the left as viewed in the FIG. 6. Now assuming that the motor drives a driving shaft 6 causing the worm wheel 8 to rotate clockwise, the cam 101 begins to pull in the wire with varying speed as the wire moves in the direction of the arrow in the FIG. 6 due to the effect of the cam shape so that the mechanical fingers grasps the object at decreased speed and the correspondingly increased torque. In this embodiment, a pair of guide rollers 103 is provided to guide the wire 102 to move along a line at a predetermined angle relative to the link divider 69.

Embodiments of the object grasping system according to the present invention are given here only by way of illustration, attention being called the fact that other variations reasonably contemplated by those skilled in the art may fall within the scope of the appended claims of the invention wherein means are provided for decreasing the sped of motion of the mechanical fingers with correspondingly increased moment.

It is also desirable to incorporate into the object grasping system control means for regulating the force exerted upon the surface of the object to be grasped by each finger, particularly when soft or destructible material are to be handled. Pressure sensors may be adapted for installation on the finger unit in a suitable manner to produce a signal to be transmitted to a power control means for feedback control. This approach would necessitate electronic control means connected with pressure sensor means installed on the necessary area of the finger unit with the result of introducing undesirable complexity and increased size and weight. To eliminate such disadvantages, a friction clutch may be used with the object grasping system according to the present invention. Such a friction clutch can be best installed on the drive shaft 6. The friction clutch so installed serves to prevent further rotation of the motor as the finger unit has completed the motion of grasp and begins to develop increasing torque on the surface of the object. Furthermore, strain gauges may be used with the second embodiment of the present invention. These are installed on the wire 94 for measuring the amount of strain developed thereon to regulate the speed of the motor through electric control means.

The structural design of the finger assembly described above is given by way of example and can take various other forms so long as the effect of grasping of objects is attainable. A glove-like cover may be used to clothe the mechanical finger assembly for protection or other purposes. A glove having enough high elasticity may be used on the mechanical finger unit to replace the compression springs 67 and 18.

Moreover, as in the second and fourth embodiment, although the non-circular gears 91 and 92 or 95 and 96 are elliptical or partially elliptical, other shapes can be used according to the particular purpose.

Thus, it will be apparent that the object grasping system is of very simple construction and effective in operation as well as practically acceptable.

What is claimed is:

1. In an object grasping system including a mechanical finger assembly operable to hold the object, a constant speed motor, a motion converting means for converting the rotary motion of said motor into linear motion, and a link mechanism for transmitting linear motion from said motion converting means to said mechanical finger assembly,
the improvement wherein the said motion converting means comprises a stepped gear having at least two circular gear trains of different pitch circle and being constantly rotated by the rotary motion of said motor; and a stepped rack joined to said link mechanism and having at least two tooth trains which trains correspond to said circular gear trains of the stepped gear and are in gear engagement therewith,
whereby said stepped rack moves linearly by the rotation of said stepped gear engaged therewith first at a higher speed then at a lower speed so that said mechanical finger assembly approaches the object at a higher speed and grasps the object at a lower speed with increased moment.

2. In an object grasping system including a mechanical finger assembly operable to hold the object, a constant speed motor, a motion converting means for converting the rotary motion of said motor into linear motion, and a link mechanism for transmitting linear motion from said motion converting means to said mechanical finger assembly, the improvement wherein the said motion converting means comprises a non-circular driving gear being constantly rotated by the rotary motion of said motor; a non-circular following gear being in gear engagement with said driving gear; a driving wheel coaxially and integrally fixed on said following gear; and a connector means being at its one end into contact with said driving wheel and connected at the other end thereof to said link mechanism, whereby said following gear is rotated by the rotation of said driving gear first at a higher speed then at a lower speed and consequently, said mechanical finger assembly approaches the object at a higher speed and grasps the object at a lower speed with increased moment.

3. The object grasping system as defined in claim 2, wherein said connector means is a wire fixed at one end to said driving wheel.

4. The object grasping system as defined in claim 2, wherein said driving wheel is a pinion and said connector means connected at its one end to said link mechanism is provided with tooth trains engaged with said pinion.

5. In an object grasping system including a mechanical finger assembly operable to hold the object, a constant speed motor, a motion converting means for converting the rotary motion of said motor into linear motion, and a link mechanism for transmitting linear motion from said motion converting means to said mechanical finger assembly,
the improvement wherein the said motion converting means comprises a cam wheel being constantly rotated by the rotary motion of said motor and a wire being at its one end into contact with said cam wheel and connected at the other end thereof to said link mechanism,
whereby said wire moves linearly first at a higher speed then at a lower speed and consequently, said mechanical finger assembly approaches the object at a higher speed and grasps the object at a lower speed with increased moment.

* * * * *